United States Patent [19]

Lequime et al.

[11] Patent Number: 4,836,674

[45] Date of Patent: Jun. 6, 1989

[54] METHOD AND APPARATUS FOR DETERMINING COLOR, IN PARTICULAR OF A DENTAL PROSTHESIS

[75] Inventors: Michel Lequime, Eguilles; Jocelyn Millet, Perthuis, both of France

[73] Assignee: Bertin & Cie, Plaisir, France

[21] Appl. No.: 96,354

[22] PCT Filed: Dec. 12, 1986

[86] PCT No.: PCT/FR86/00433

§ 371 Date: Aug. 13, 1987

§ 102(e) Date: Aug. 13, 1987

[87] PCT Pub. No.: WO87/03470

PCT Pub. Date: Jun. 18, 1987

[30] Foreign Application Priority Data

Dec. 13, 1985 [FR] France ................... 8518540

[51] Int. Cl.$^4$ ............................ G01J 3/42; G01J 3/36
[52] U.S. Cl. .................................. 356/319; 356/323; 356/328; 433/26
[58] Field of Search ............... 356/319, 323, 325, 326, 356/328, 405; 433/26

[56] References Cited

U.S. PATENT DOCUMENTS

| | | | |
|---|---|---|---|
| 3,986,777 | 10/1976 | Roll | 356/418 |
| 4,029,391 | 6/1977 | French | 356/418 |
| 4,125,329 | 11/1978 | French et al. | 356/418 |
| 4,131,367 | 12/1978 | French et al. | 356/418 |
| 4,375,919 | 3/1983 | Busch | 356/328 |
| 4,654,794 | 3/1987 | O'Brien | 356/326 |

FOREIGN PATENT DOCUMENTS

| | | |
|---|---|---|
| 1470766 | 2/1967 | France . |
| 2188157 | 1/1974 | France . |
| 2231958 | 12/1974 | France . |
| 2359406 | 2/1978 | France . |
| 2376087 | 7/1978 | France . |
| 2516785 | 5/1983 | France . |
| 87/02454 | 4/1987 | PCT Int'l Appl. ............... 356/326 |

Primary Examiner—F. L. Evans
Attorney, Agent, or Firm—Dennison, Meserole, Pollack & Scheiner

[57] ABSTRACT

The invention can be used to determine the color to be given to a dental prosthesis, for example, on the basis of color measurements performed on adjacent teeth in the mouth of the patient. An optical fiber instrument picks up light reflected from a tooth and transmits it to the inlet of a spectrocolorimeter which associated with a microprocessor in order to determine the diffuse spectral reflectance of the tooth and to calculate the tristimulus values of its apparent color under various different types of illumination. The invention is particularly suitable for determining the color of dental prostheses.

9 Claims, 1 Drawing Sheet

METHOD AND APPARATUS FOR DETERMINING COLOR, IN PARTICULAR OF A DENTAL PROSTHESIS

The invention relates to a method and to apparatus for determining the color to be given to an object, in particular a ental prosthesis, on the basis of the color of another object, in particular the adjacent teeth in the mouth of the patient.

BACKGROUND OF THE INVENTION

It is essential for a dental prosthesis (e.g. a crown, a bridge, an implant, etc.,) to be as close as possible in color to the adjacent teeth.

At present, the color of a dental prosthesis is determined at sight, in general by a dentist comparing color samples with the teeth of the patient. This procedure gives results that necessarily depend on the dentist's capacity to distinguish between colors which are very similar, which is sufficient reason for results that are not always very satisfactory.

It may also happen that a prosthesis color selected in this way is very close to the color of the adjacent teeth so long as the teeth are illuminated by a light source giving a generally uniform spectrum, but that the prosthesis color appears quite different when the teeth are illuminated by a light source such as a fluorescent tube which radiates a spectrum concentrated in a few lines (a phenomenon sometimes known as metamerism).

Colorimeters exist which measure the color of an object by using filters to determine the tristimulus values X, Y, and Z of the object's color, thereby enabling said color to be reproduced by mixing three primary colors. However, a knowledge of the tristimulus values applicable for any given illumination is not sufficient for specifying the values under different illumination. Thus, in order to obtain good results using colorimeters it is necessary to take a large number of color measurments under different lighting conditions, which is a considerable problem.

The invention seeks to mitigate this problem.

An aim of the invention is to provide a method and apparatus for determining the apparent colors of an object corresponding to various different types of illumination, on the basic of a single measurement performed under unspecialized illumination.

Another aim of the invention is to provide a method and apparatus of the above-mentioned type suitable for performing such measurements on objects which are difficult of access, such as a person's teeth.

SUMMARY OF THE INVENTION

The present invention provides a method of determining the color, in particular of a dental prosthesis, with reference to the color of an identical object such as adjacent teeth in the mouth of a patient, the method consisting in: picking up color information in situ by means of one or more optical fibers suitable for being inserted into the mouth of the patient to pick up light reflected from a tooth adjacent to the emplacement for the prosthesis; in transmitting the reflected light by optical fiber to a spectrocolorimeter; and in determining the diffuse spectral reflectance $D(\lambda)$ of the tooth, and then in calculating the various apparent colorations of the tooth corresponding to different types of light by which it may be illuminated, in order to define the prosthesis color having the best possible match from the esthetic point of view with the adjacent teeth.

After being suitably sampled, the diffuse spectral reflectance of the illuminated tooth can be used to calculate the tristimulus values of the tooth's coloration under any possible type of illumination; and in practice this is done for standardized types of light source representative of various possible types of illumination (e.g. an equal energy source, C.I.E. standard illuminants, a spectrum line source, etc.).

The invention thus makes it possible to obtain the tristimulus values of the apparent colors of a tooth under different types of illumination from a single measurement, and thereby makes it possible to select a prosthesis color with tristimulus values that are as close as possible to those of the apparent colors of the tooth.

Diffuse spectral reflectance measurements may be performed, and the apparent colors may be determined for several of the patient's teeth and for several prosthesis color test samples, thereby enabling the sample whose apparent colors are closest to those of the patient's teeth to be determined.

Advantageously, when determining which prosthesis color to use, more weight is given to appearance under daylight than under other types of illumination.

The invention can also be used to display an image on a graphics screen showing the colors of a set of adjacent teeth (including both natural teeth and prosthesis teeth) as they would appear under various different types of illumination.

It is thus possible to verify whether the selected prosthesis color is a good match to the color of the patient's other teeth under different lighting conditions.

The invention also provides apparatus for determining the color to be given, in particular to a dental prosthesis with reference to the color of at least one adjacent tooth in the mouth of a patient, said apparatus comprising: an instrument for picking up color information in situ, said instrument being suitable for insertion into the mouth of the patient and including optical fiber means for picking up and for transmitting light reflected by a tooth; a spectrocolorimeter having an optical fiber input path connected to said pick-up and transmission means, said spectrocolorimeter including means measuring and determining the diffuse spectral reflectance of the tooth; and calculating means associated with the spectrocolorimeter for determining the various apparent colorations of the tooth corresponding to different types of illumination.

The instrument for picking up color information includes an optical fiber associated with a light source for illuminating the tooth, together with an optical fiber for picking up and for transmitting the light reflected by the tooth, with optical focusing means enabling local measurements to be performed on a portion of a tooth, and/or with means for homogenizing the incident or the reflected light, e.g. an integrating microsphere.

Advantageously, the spectrocolorimeter is of the type comprising a spectrometer having a mosaic of photodetector elements associated with a microprocessor and mounted on an optoelectronic card which also mounts at least two optical fiber measurement paths leading to the inlet of the spectrometer and provided with shutters for switching the measurement paths, with means for calibrating the photodetector wavelengths, and electronic circuits for reading the photodetectors.

One of the spectrometer measurement paths may then be associated with the light source, while the other measurement path is connected to the instrument for picking up color information in order to receive light reflected by the illuminated tooth.

The microprocessor may be associated with a graphics terminal in order to display sets of adjacent teeth (including both natural teeth and prosthesis teeth), and to show their colors as they would appear under different types of illumination.

BRIEF DESCRIPTION OF THE DRAWING

In the following description given by way of example, reference is made to the accompanying drawing, in which.

DESCRIPTION OF THE PREFERRED EMBODIMENT

Figures 1, 2:
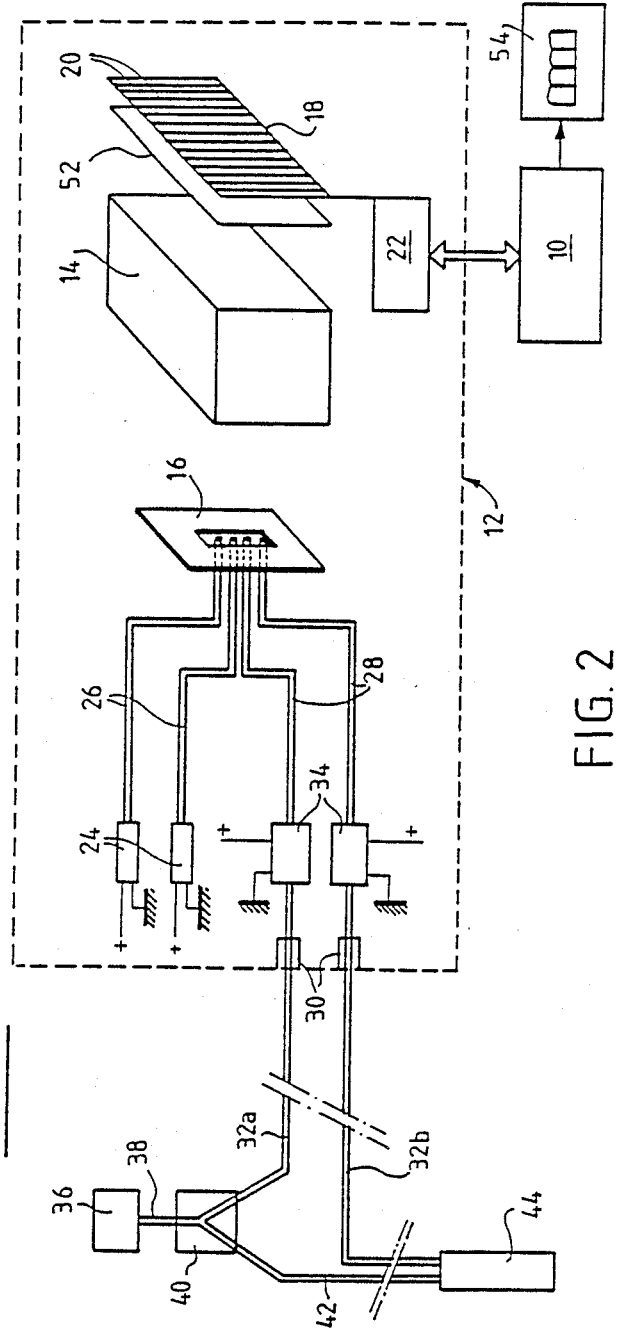
FIG. 1 is a diagrammatic view of an apparatus in accordance with the invention.
FIG. 2 is a diagrammatic view on a larger scale of a color information pick-up instrument shown facing a tooth.

In the embodiment shown in FIG. 1, the apparatus in accordance with the invention is essentially constituted by associating a spectrocolorimeter of the type described in French patent application No. 85 15351 filed Oct. 16, 1985, with an instrument for picking up light in situ, together with an unspecialized light source.

The spectrocolorimeter is essentially constituted by associating a control microprocessor 10 and an optoelectronic card 12 whose outline is represented in dashed lines and on which there are mounted: a diffraction grating type spectrometer 14, for example using Littrow type optics including an inlet slot 16 and a strip 18 of photodetectors 20 which may, for example, be silicon photodiodes.

These photodetectors 20 are associated with electronic circuits given a general reference 22 which are mounted on the card 12 and which include: circuits, e.g. multiplex type circuits, for reading detector charge; an analog-to-digital converter; a programmable clock for determining the integration time of the photodetectors 20; buffer memories; and circuits for processing the digitized data.

The card 12 also carries means for calibrating the photodetectors 20 in wavelength, which means are constituted in this case by two light-emitting diodes (LEDs) 24, which are DC powered under the control of the microprocessor 10 and which are connected to the inlet slot 16 of the spectrometer via optical fibers 26 constituting two calibration paths. Each LED 24 emits light radiation of a given wavelength when powered, and the radiation wavelengths of the two LEDs are suitably far apart from each other in the visible spectrum.

Two optical fiber measurement paths 28 are also provided on the card 12, with one end of each measurement path being disposed at the inlet slot 16 to the spectrometer, and with the other end of each measurement path being connected via a connector 30 mounted on the card 12 to a measurement path 32a, 32b formed by an optical fiber which may be very long, if so desired.

Each measurement path 28 mounted on the card 12 is also fitted with a shutter 34 which is DC powered under the control of the microprocessor 10 and which serves to open or close the corresponding measurement path 28.

A light source 36 which may be constituted, for example, by a lamp emitting reference spectrum radiation, is connected via an optical fiber 38 and a Y-coupler 40 firstly to the input of the measurement path 32a of the spectrometer 12, and secondly via an optical fiber 42 to a light pick-up instrument 44 which is also connected to the other spectrometer measurement path 32b.

The instrument 44 contains two optical fibers 46 and 48 with are respectively connected to the optical fibers 42 and 32b or which are constituted by extensions thereof, and which open out freely at the end of the instrument 44. In practice, the instrument 44 is in the form of a dental instrument with a diameter of a few millimeters so that it can be easily inserted into the mouth of a patient and brought up to a tooth 50.

The instrument 44 may optionally include light focusing means (not shown) enabling local information to be obtained from a point on a tooth. The instrument may also include means for homogenizing the incident or the reflected light, e.g. an integrating microsphere associated with the fiber 46 or 48, thereby overcoming variations due to varying incidence. Optical information may be picked up using a 0/45 or a 45/0 geometry (incident light normal, reflected light at 45°, or *vice versa*) or using a O/d or a d/O geometry (incident light normal and reflected light taken up by the microsphere, or *vice versa*).

Further, as already described in French patent application No. 85 15351, the ends of the optical fibers forming the measurement paths 28 and the calibration paths 26 are superposed on one another in the inlet slot 16 to the spectrometer. The detectors 20 must therefore be of adequate height, i.e. their height must correspond to the height of the superposed ends of the optical fibers. When the spectrometer 14 uses Littrow optics having a magnification ratio of 1/1, the height of the detectors 20 must be not less than the height of the superposed ends of the four optical fibers constituting the measurement and calibration paths, in other words the height must be equal to four times the diameter of a single optical fiber.

Further, a graduated density compensation filter 52, referred to as a focal plane corrector, is placed over the photodetectors 20 so that they all receive energy flux of the same order of magnitude, and preferably so that they all receive substantially equal energy flux.

Optical fibers transmit poorly in the blue region of the spectrum, so that the energy flux of spectrum components entering the spectrometer in the blue is much less than the energy flux of the red components, and attenuation also increases with increasing length of the optical fibers constituting the measurement paths. The focal plane corrector 52 serves to reestablish substantially uniform energy flux over the photodetectors 20. Further, its use is preferable to the use of a set of blue filters which pass only a fraction of the incident energy flux.

The above-described apparatus operates as follows:

The operations of calibrating the photodetectors 20 may be performed automatically in a periodic manner under the control of the microprocessor 10, or else on user request. To do this, the shutters 34 on the measurement paths 28 are closed and measurements are performed by turning on one of the LEDs 24 while the other is off, and then by turning on the other LED 24 while the first is off. These measurements are repeated regularly at predetermined time intervals of given length, with the results of the first measurements being stored in memory and compared with the results of subsequent measurements, in order to verify that they match and to automatically recalibrate the strip of photodetectors 20, if necessary.

In order to perform a spectrum measurement, both LEDs 24 are held off, and one of the measurement paths 28 is opened while the other measurement path 28 is closed. The energy flux received by the photodetectors 20 is measured and compared with the saturation threshold, in order to determine the time during which the photodetector should integrate the received signal so as to obtain as large a singal as possible below the saturation threshold. In general, the integration time varies between about one second and one millisecond, and it is determined by a programmable clock, thereby making it possible to automatically match the integration time to the value of the received energy flux so as to obtain a signal representing 90% of the dynamic range of the photodetectors.

The signals from the detectors 20, i.e. the charges thereon, are read by multiplex type read circuits, operating at a constant read frequency equal to the maximum red frequency for the detectors of the strip, i.e. the frequency which corresponds to the minimum value of the integration time. When the photodetectors are read, the integration is reset to zero for the next measurement. The signals read from the detectors are digitized by an analog-to-digital converter, and are then processed. Photodetector noise is measured by closing all of the measurement paths. The measured noise is automatically substracted from the measurement signal obtained by opening a measurement or a reference path.

The order to determine the apparent colorations of a tooth, the following procedure is followed:

The light pick-up instrument 44 is placed in the patient's mouth opposite the zone of tooth whose color is to be determined. The tooth is illuminated by the light source 36 via the optical fiber 42, 46 which ends at the end of the instrument 44 facing the tooth 50. The light reflected by the tooth is modified by the color of the tooth and is picked-up by the optical fiber 48 and is then transmitted by the measurement path 32b to the inlet slot 16 of the spectrometer 14.

Initially, the measurement path 32a associated with the lamp 36 is open in order to perform a spectrometric measurement of the radiation emitted by the lamp, while the measurement path 32b associated with the tooth 50 is closed. Then the measurement path 32a is closed while the measurement path 32b is opened in order to perform a spectrometric measurement of the light reflected by the tooth 50. The ratio of these two measurements is used to determine the diffuse spectral reflectance $D(\lambda)$ of the tooth.

The tristimulus values X, Y, and Z of the color of the tooth are determined using the following equations:

$$X = \int_\lambda D(\lambda)S(\lambda)x(\lambda)d\lambda$$

$$Y = \int_\lambda D(\lambda)S(\lambda)y(\lambda)d\lambda$$

$$Z = \int_\lambda D(\lambda)S(\lambda)z(\lambda)d\lambda$$

where:

$\lambda$ is wavelength, $D(\lambda)$ is the diffuse reflectance, $S(\lambda)$ is a spectral coefficient depending on the illumination source, and $\bar{x}(\lambda)$, $\bar{y}(\lambda)$, and $\bar{z}(\lambda)$ are the spectral tristimulus values for the C. I. E. colorimetric reference observer.

The chromaticity co-ordinates x, y, and z of the color of the tooth are given by the following equations:

$$x = X/(X + Y + Z)$$

$$y = Y/(X + Y + Z)$$

$$z = Z/(X + Y + Z)$$

While the diffuse spectral reflectance $D(\lambda)$ is available, wavelength sampling is performed step-by-step over a range of 5 nm to 10 nm, for example, and the tristimulus values X, Y, and Z are calculated using the above equations for a corresponding value of $S(\lambda)$. The $S(\lambda)$ curves for standardized reference light sources are known at the same sample intervals as are used for sampling $D(\lambda)$, as are the sampled values of $\bar{x}(\lambda)$, $\bar{y}(\lambda)$, and $\bar{z}(\lambda)$.

It is thus possible to determine the tristimulus values of the apparent colorations of a tooth under various different lighting conditions from a single measurement of its diffuse spectral reflectance.

The same operations can be repeated by placing the end of the pick-up instrument 44 opposite prosthesis color test samples, of the kind kept by dentists and prosthesis makers. By comparing the results obtained, i.e. the apparent colorations under different types of lighting, it is possible to determine which one of the test samples is closest in color to the tooth under different types of illumination. In practice, when performing such comparisons, most weight is given to the colors that appear under natural light.

These operations of determining the diffuse spectral reflectance and of calculating the tristimulus values can naturally be performed for other zones of a patient's tooth or for other teeth adjacent to the prosthesis.

The results of these measurements and of these calculations can be displayed on a graphics terminal 54 associated with a microprocessor 10, with a set of teeth being displayed on the terminal having the same shapes as the patient's teeth and as the prosthesis teeth, and having colors that correspond to the apparent colors as determined for various different types of lighting. This display makes it possible to check very quickly whether a pleasing color match has been obtained between the test samples and the patient's own teeth.

Apparatus in accordance with the invention can thus be used in a rapid and reliable manner to determine which color should be used for a dental prosthesis, as a function of the color of the teeth which are adjacent to the prosthesis in the mouth of the patient.

Dental prostheses are often made of resin which is colored by pigments which are embedded therein quantities that vary as a function of the color to be obtained. The invention can be used not only to determine the color to be given to the resin to a high degree of accuracy, but also to determine the corresponding quantities of pigment, and thus to automate the resin-preparing process.

The invention is also applicable to other technical fields in which the color of one article must be matched to the color of another.

We claim:

1. A method for determining a color for a dental prosthesis by referencing the color of an adjacent tooth in the mouth of a patient, comprising the steps of:

inserting instrument means hving at least one optical fiber in the mouth of the patient;

illuminating through the instrument means at least one tooth adjacent to an area of emplacement for a dental prosthesis;

picking up through the instrument means color information formed by the illuminating light reflecting off the adjacent tooth;

transmitting through the optical fiber the reflected light to a spectrocolorimeter;

determining a diffuse spectral reflectance of the adjacent tooth;

calculating various colorations for the dental prothesis from the diffuse spectral reflectance, the various colorations corresponding to different types of light by which the dental prothesis may be illuminated; and displaying a set of teeth representing the adjacent tooth and the dental prothesis with respective colorations under the different types of light.

2. The method according to claim 1, wherein said steps of calculating and displaying of the apparent colorations for the dental prothesis and the adjacent tooth are repeated for a plurality of color test samples to determine which sample has apparent colorations closest to the apparent colors of the adjacent tooth.

3. The method according to claim 1, further comprising the steps of:

performing a spectrometric measurement with light emitted from a light source;

performing a spectrometric measurement with the reflected light from the adjacent tooth; and determining the diffuse spectral reflectance of the adjacent tooth using the ratio of the two spectrometric measurements.

4. A method according to claim 1, wherein most weight is given to the apparent color of the prosthesis under natural light when defining the color of the prosthesis.

5. A method according to claim 1, wherein the set of teeth representing the prosthesis and the adjacent tooth of the patient are displayed on a graphics terminal to show their respective apparent colors.

6. An apparatus for determining a color for a dental prosthesis by referencing the color of at least one adjacent tooth in the mouth of a patient, said apparatus comprising:

instrument means, suitable for insertion into the mouth of a patient, for picking up color information of a tooth adjacent an area of emplacement of a dental prosthesis;

optical fiber means associated with said instrument means for illuminating the adjacent tooth and for picking up reflected light from the adjacent tooth;

a spectrocolorimeter having an optical fiber path connected to said optical fiber means for receiving the reflected light from said optical fiber means, said spectrocolorimeter including means for measuring and determining diffuse spectral reflectance of the adjacent tooth;

calculating means associated with said spectrocolorimeter for determining, under different types of illuminations, various apparent colorations of the adjacent tooth; and a graphics display terminal for displaying the dental prothesis and the adjacent tooth as a set of teeth with respective apparent colorations, wherein the color of the dental prothesis is chosen from a plurality of displayed color test samples.

7. Apparatus according to claim 6, wherein said instrument means for picking up color information includes an optical fiber associated with a light source for illuminating the tooth, together with an optical fiber for picking up and for transmitting the light reflected by the tooth.

8. Apparatus according to claim 6, wherein the spectrocolorimeter is of the type comprising a spectrometer having an inlet and a mosaic of photodetector elements associated with a microprocessor and mounted on an optoelectronic card which also mounts at least two optical fiber measurement paths leading to the inlet of the spectrometer and provided with shutters for switching the measurement paths, means for wavelength calibrating the photodetector element, and electronic circuits for reading the photodetector element.

9. Apparatus according to claim 8, wherein one of the spectrometer measurement paths is associated with a light source and wherein the other measurement path is connected to the instrument means for picking up color information for receiving light reflected by the illuminated tooth.

* * * * *